United States Patent [19]

Whittemore

[11] Patent Number: 5,028,789
[45] Date of Patent: Jul. 2, 1991

[54] SYSTEM AND APPARATUS FOR NEUTRON RADIOGRAPHY

[75] Inventor: William L. Whittemore, La Jolla, Calif.

[73] Assignee: General Atomics, San Diego, Calif.

[21] Appl. No.: 398,748

[22] Filed: Aug. 25, 1989

[51] Int. Cl.$^5$ .......................................... G01N 23/05
[52] U.S. Cl. ........................... 250/390.02; 250/390.1; 250/494.1; 250/505.1
[58] Field of Search ............ 250/390.02, 390.1, 493.1, 250/505.1, 494.1

[56] References Cited

U.S. PATENT DOCUMENTS

| | | | |
|---|---|---|---|
| 4,582,999 | 4/1986 | Dance et al. | 250/390.1 |
| 4,599,515 | 7/1986 | Whittemore | 250/390 |
| 4,853,550 | 8/1989 | Schulz | 250/493.1 |

OTHER PUBLICATIONS

Alger et al., "A High Resolution Thermal-Neutron Radiography Facility", Nucl. Tech., 17 (2), Feb. 1973, pp. 189-192.

J. Stokes et al., A New Accelerator-Based Neutron Radiography System, Instrumentation Research Technology Corporation, Dec. 9, 1981.

*Primary Examiner*—Carolyn E. Fields
*Attorney, Agent, or Firm*—Nydegger & Associates

[57] ABSTRACT

An apparatus for use in neutron radiography has a convergent collimator of moderator material joined coaxially to a divergent collimator made of neutron-absorbing material. An aperture is formed between the collimators. The divergent collimator substantially defines a neutron beam. An imaging plane is disposed within the neutron beam. The convergent collimator has a base which defines a source plane. Neutron-emitting radioisotopes which are a source of neutrons are placed symmetrically about the source plane. Neutron-moderating material is placed between the neutron sources and the aperture. The convergent-divergent shape of the collimators is designed to expose all of the source plane for optimum and uniform thermal neutron irradiation of the imaging plane. The neutron sources are placed within the moderator at a predetermined distance from the source plane to provide maximum thermal neutron flux through the aperture to the imaging plane, while at the same time preventing direct line-of-sight gamma radiation from the neutron sources to the imaging plane.

17 Claims, 3 Drawing Sheets

SYSTEM AND APPARATUS FOR NEUTRON RADIOGRAPHY

FIELD OF THE INVENTION

The present invention relates to neutron radiography. More specifically, the present invention pertains to neutron radiography of the type using a decaying nuclear isotope as the neutron source. The present invention is particularly, though not exclusively, useful for neutron radiography in which a collimated beam of neutrons is directed through an object onto an imaging plane to generate an image of the object, to determine certain material characteristics of the imaged object.

BACKGROUND OF THE INVENTION

Neutron radiography is a non-destructive testing process used for determining certain material characteristics. In its simplest terms, neutron radiography is accomplished by irradiating an object with neutrons and measuring the resulting flux of neutrons which pass through the object per unit area. Material variations and characteristics of the tested object may thereby be detected by observing variations in neutron flux through the object. Neutron radiography is most often accomplished using thermal neutrons, or those neutrons having an average kinetic energy of about twenty-five one thousandths electron volts (0.025 eV). Some applications of neutron radiography require the use of cold neutrons, or neutrons having a kinetic energy less than five one thousandths electron volts (0.005 eV). Other applications may require the use of epithermal neutrons, or neutrons having kinetic energies up to a few electron volts. Neutrons with any of these energy levels are usually produced by thermalizing, or "moderating", high energy neutrons (up to several MeV), known as fast neutrons, which are emitted by a neutron source. This moderation is accomplished by directing the fast neutrons through a moderating material. The thermalization process results in an energy spectrum of neutrons essentially in thermal equilibrium with the moderating material.

Several different types of fast neutron sources for radiography are used. For example, nuclear reactors are one source of neutrons which provide highly intense beams of neutrons for irradiating an object to be tested. For many important applications of neutron radiography, however, it is desirable to have a neutron source other than a nuclear reactor.

An alternative source of neutrons known in the prior art is a Van de Graff accelerator. It produces neutrons for irradiation by accelerating deuterons against a beryllium target to produce fast neutrons. The beryllium target is disposed in a chamber of moderator material appropriate for moderating, or thermalizing, the fast neutrons down to the desired neutron energy level for radiography. An example of such a device is discussed in U.S. Pat. No. 4,599,515 which issued to Whittemore.

Yet other sources of neutrons for radiography are radioisotopes. One such radioisotope is californium-252, which emits, by radioactive decay, approximately $10^6$ neutrons per second per microgram of californium. The seemingly large neutron flux produced by californium-252 and other radioisotopes, however, is still much less intense than the neutron flux produced by a nuclear reactor. It is, therefore, important to make optimum use of all available neutrons when using a radioisotope neutron source in order to obtain a good image with a minimum of exposure time. A neutron radiography device using a radioisotope as the neutron source may incorporate one or several design features to fulfill the requirement of optimum use of available neutrons. For example, as is well known in the art, neutron flux will vary throughout the radiography device. The radiography apparatus could be designed to establish a maximum thermal neutron flux at the imaging plane. One way of achieving this result is to dispose the radioisotope sources in a neutron moderator such that the imaging plane is exposed to the maximum thermal neutron flux in the moderating material. A second method of making optimum use of available neutrons is to shield the imaging plane from non-neutron radiation "noise". Such noise primarily consists of electromagnetic radiation, such as gamma rays produced by source radioisotope decay. The gamma rays, by irradiating the imaging plane, can thereby lower system photographic contrast. In the past, conventional radioisotope neutron radiography devices have provided poor shielding of gamma rays emerging directly from the radioisotopes. This is due, in part, to some of these prior devices disposing the neutron source in line-of-sight of the imaging plane, in an attempt to obtain maximum neutron flux. Unfortunately, such line-of-sight placement also results in a substantial amount of direct gamma irradiation of the imaging plane.

A third design technique to optimize the number of available neutrons in a radiograph is to establish a uniform neutron flux across the imaging plane by opening up the full neutron source plane as an optimum source of neutron flux. By establishing a substantially uniform neutron flux across the entire imaging plane, a greater area of the test object per exposure may be radiographed. Conventional designs for neutron radiography devices which use radioisotopes as the neutron source tend to produce a neutron flux which is not uniform across a relatively large imaging plane. This, in turn, either reduces the effective area of the test object which can be radiographed with each exposure, or results in lower photographic image density of those parts of the imaged object or objects near the boundaries of the imaging plane.

Accordingly, it is an object of the present invention to provide a neutron radiography deice which optimizes neutron flux across the imaging plane. It is a further object of the present invention to provide a neutron radiography device which produces a uniform neutron flux across the imaging plane. Still another object of the present invention is to provide a neutron radiography device which accomplishes the above while substantially shielding gamma rays from the imaging plane. Another object of the present invention is to provide a neutron radiography device that is durable, reliable, and cost-effective in its manufacture and use.

SUMMARY OF THE INVENTION

A preferred embodiment of the neutron radiography apparatus comprises an imaging plane and a source of neutrons disposed on one side of the plane. The neutron source is preferably a plurality of nuclear isotopes which produce neutrons by radioactive decay. The apparatus uses a convergent-divergent collimator system comprised of a convergent collimator joined coaxially with a divergent collimator, the joined collimators having a central axis. The convergent collimator is formed within a neutron moderating material and has a base and converging walls disposed toward an aperture. The divergent collimator has diverging walls of neutron and electromagnetic radiation-absorbing material which extend from the aperture toward an expanded or divergent end. The convergent-divergent collimator is disposed between the neutron source and the imaging plane. The divergent end of the divergent collimator directs neutrons through an object to be imaged to an imaging plane or planes. The base of the convergent collimator defines a thermal neutron source plane. In the preferred embodiment, the base and the aperture are square. The neutron source comprises a plurality of radioactive isotopes disposed in the plane of the base symmetrically about the central axis. The configuration of the collimators and the positioning of the isotopes allow for an optimum amount of neutron moderator to be placed between the fast neutron sources and the aperture. Stated differently, the fast neutron-producing radioisotopes are positioned an optimum distance from the central axis within the neutron moderator for maximizing thermal neutron flux at the source plane. This, in turn, produces a maximum thermal neutron flux through the aperture and onto the imaging plane. The convergent collimator portion further opens up the full source plane as a source of thermal neutron flux, while also providing for greater distance between the neutron-absorbing walls at the aperture and the neutron source plane.

A collar of neutron poison may be positioned to surround the aperture at the junction between the convergent and divergent collimators to control neutron leakage and define a focused neutron beam to irradiate the imaging plane. In addition, the location of the source isotopes about the central axis is such that the radiation shielding surrounding the divergent collimator may be physically placed between the sources and the imaging plane. This placement shields the imaging plane from a substantial amount of gamma radiation produced by source radioisotope decay.

To shield the imaging plane further from unwanted electromagnetic radiation, an electromagnetic radiation filter may be disposed at the base of the convergent collimator. This additional shield further attenuates electromagnetic radiation, such as that produced by secondary nuclear interactions between neutrons and hydrogenous and other materials within the apparatus.

The novel features of this invention, as well as the invention itself, both as to its structure and its operation, will be best understood from the accompanying drawings, taken in conjunction with the accompanying description, in which similar reference characters refer to similar parts, and in which:

DETAILED DESCRIPTION OF THE PREFERRED EMBODIMENT

Figure 1:
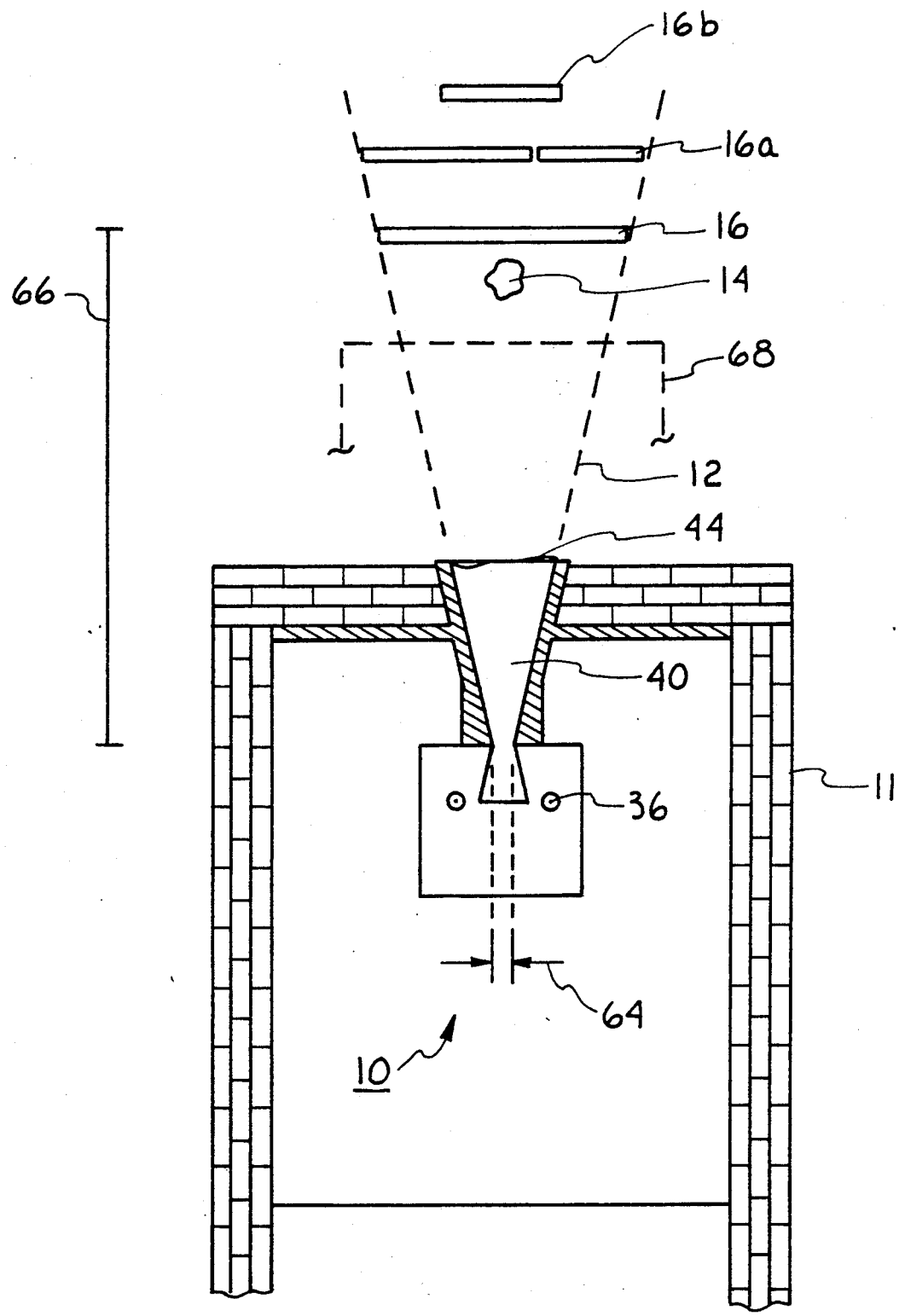
FIG. 1 is a perspective view of the neutron radiography apparatus in its intended environment in accordance with the present invention.

Referring now to FIG. 1, there is shown a neutron radiography apparatus, generally designated 10, in its intended environment. Neutron radiography apparatus 10 is encased in outer shield 11. Outer shield 11 may be composed of any suitable material, such as concrete. As shown in FIG. 1, neutron radiography apparatus 10 directs or channels a collimated beam 12 of neutrons emanating from apparatus 10 through object 14 onto an imaging plane, designated 16. Imaging plane 16 is preferably an array of one or more film cassettes or a real-time electronic imaging detector for making a neutron-generated image of the object 14. As shown in FIG. 1, imaging plane 16 may be positioned anywhere within beam 12. Imaging plane 16a is an embodiment of imaging plane 16 which comprises a plurality of film plates. Imaging plane 16b is yet another embodiment of imaging plane 16 which comprises a film plate or real-time electronic imaging camera that is not exposed to the full extent of beam 12. The distance imaging plane 16 is placed from aperture 30, designated 66 in FIG. 1, will vary according to the particular application of device 10. This is because system photographic resolution depends on the ratio of distance 66 to the width 64 of aperture 30. It will be understood by the skilled artisan that as distance 66 is increased in relation to width 64, system photographic resolution is increased. Because width 64 is usually fixed in response to other design considerations discussed more fully below, distance 66 is generally the only variable available to the operator with which to establish system resolution. However, the benefits of increased system resolution obtained by increasing distance 66 must be balanced against the corresponding decrease in neutron flux intensity at imaging plane 16. As can be readily appreciated, the thermal neutron flux at imaging plane 16 decreases in inverse proportion to the square of distance 66. Therefore, the operator will establish a distance 66 which conforms to the objectives of the particular application of neutron radiography device 10. For most applications of radiography device 10, distance 66 is at least twenty (20) times greater than width 64.

As will be further appreciated by those skilled in the art, certain steps may be taken to ameliorate the effects of an increased distance 66 on neutron flux intensity upon imaging plane 16, as discussed above. For example, still referring to FIG. 1, a container 68 of helium gas may be placed partially or completely within neutron beam 12 between imaging plane 16 and divergent end 44 of divergent collimator 40. As is well known in the art, neutrons are exposed to approximately one and a half percent (1.5%) less scattering (hence removal) interactions in helium, per foot of travel, than in air. Thus, fewer neutrons will be scattered out of beam 12 if beam 12 is directed through helium, as discussed above, instead of air. This, in turn, will result in an increased neutron intensity with which to irradiate imaging plane 16.

Figure 2:
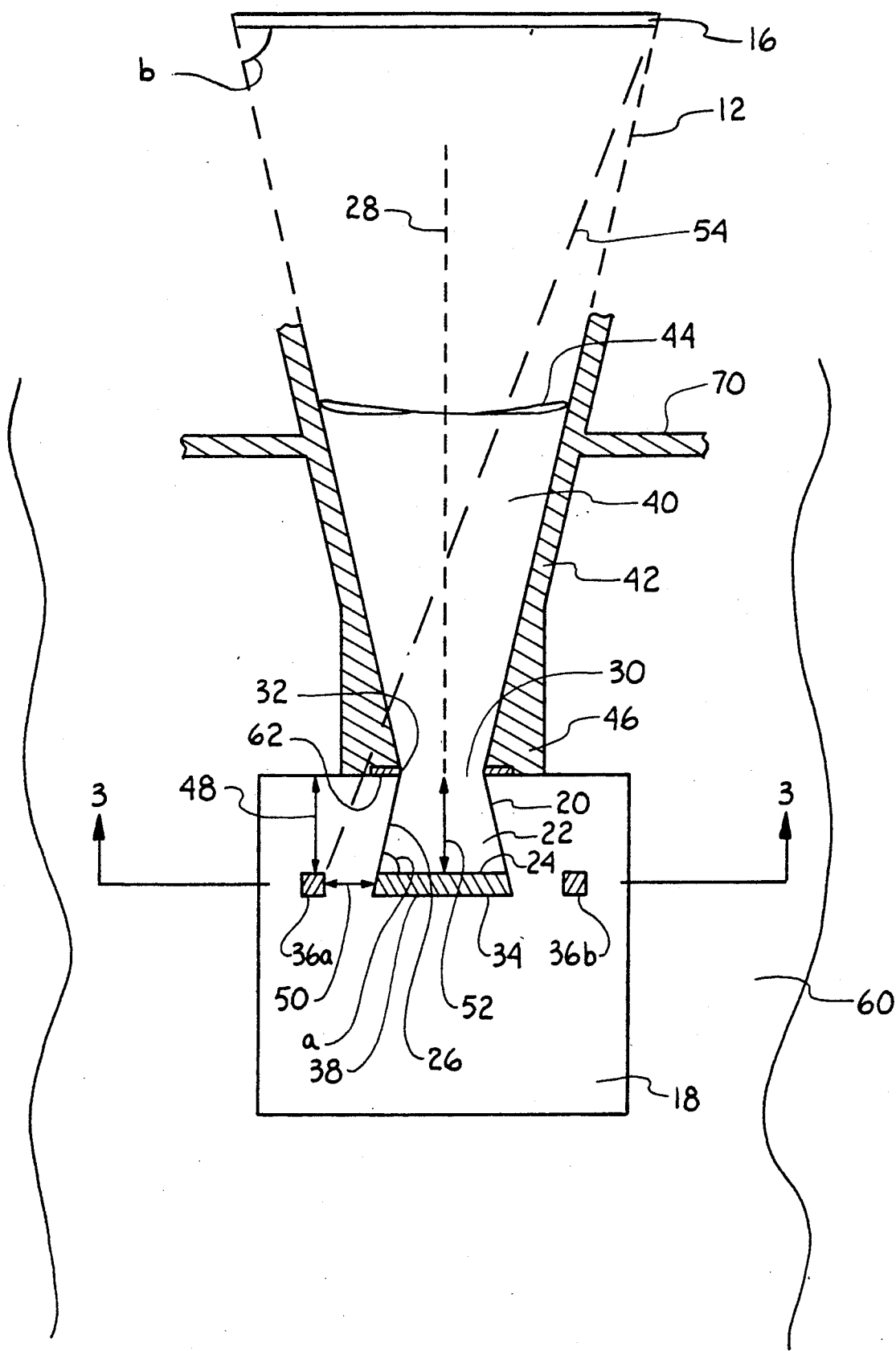
FIG. 2 is a cross-sectional view of the neutron radiography apparatus according to the present invention.

The components of apparatus 10 can perhaps best be appreciated further with reference to FIG. 2. In particular, apparatus 10 includes a high density polyethylene moderator 18. As earlier mentioned, moderator 18 moderates fast neutrons which are emitted from radioisotope neutron sources to thermal energies A convergent collimator 20 is formed in moderator material 18. In particular, convergent collimator 20 is comprised of moderator 18 having a hole 22 defining a convergent collimator cavity. The cavity or hole 22 has a bottom or base 24, and convergent walls 26. Base 24 preferably lies in a plane parallel to imaging plane 16. Convergent walls 26 extend from generally flat base 24 and converge toward a central axis 28, which axis 28 is generally perpendicular to imaging plane 16. Converging walls 26 are tapered toward an aperture 30 and terminate at an aperture periphery 32. Walls 26 form an acute angle "a" with base 24. Base 24 has a layer 34 of gamma ray-attenuating material which is selected to have a minimum thermal neutron absorption cross section. Layer 34 may be positioned anywhere within convergent collimator 20 or aperture 30. However, the layer 34 is positioned at base 24 in the preferred embodiment to minimize the effects of the thermal neutron scattering caused by layer 34. Stated differently, by placing layer 34 at base 20, as many neutrons are scattered into neutron beam 12 by layer 34 as are scattered out of neutron beam 12 by layer 34. Preferably, in the embodiment shown, the layer 34 at base 24 comprises a bismuth (Bi) filter approximately one (1) inch thick. In the preferred embodiment, layer 34 is comprised of one or more substantially pure bismuth crystals. As also may be appreciated with reference to FIG. 3, source plane 38 is a square shape in the preferred embodiment, as is aperture periphery 32. Positioned symmetrically about base 24 are a plurality of fast neutron-emitting sources generally designated 36. In the embodiment shown, the sources 36 are coplanar with base 24. In this embodiment, there are eight (8) neutron sources, but any number may be utilized provided they are positioned substantially symmetrically about base 24 to generate neutron flux at base 24.

Coaxially joined with convergent collimator 20 at aperture periphery 32 is a divergent collimator 40. Divergent collimator 40 has diverging walls 42 extending from aperture periphery 32 toward a divergent or expanded distal opening or end 44. Divergent collimator 40 channels beam 12 of thermal neutrons toward imaging plane 16. In the embodiment shown, divergent collimator walls 42 form an acute angle "b" of approximately seventy-five degrees (75°) with imaging plane 16. Angle "b" is established to expose the entire area of imaging plane 16 with neutrons all of which emanate from source plane 38, explained in greater detail below. In the preferred embodiment, angle b is substantially equal to angle a. Also, divergent end 44 preferably has a square periphery which corresponds to the shape of aperture 30 and base 24. Diverging walls 42 of divergent collimator 40 are made of neutron-absorbing material (poison) and electromagnetic radiation-absorbing material. Divergent collimator walls 42 thus act as a radiation shield. Specifically, divergent collimator 40 material preferably comprises both a neutron poison and a gamma ray attenuator, such as a combination of lead (Pb) shot and boron glass (B) frit. Divergent walls 42 are formed with wall extensions 70 which extend from walls 42 and which are substantially perpendicular to axis 28. In the preferred embodiment, wall extensions 70 are positioned between imaging plane 16 and sources 36 and as far from sources 36 as practicable, to allow for the placement of a larger volume of moderator 18 around sources 36. In addition, divergent collimator 40 has a bottom wall portion 46 which extends toward aperture 30 as shown in FIG. 2. Disposed within bottom wall 46 and surrounding aperture periphery 32 is high efficiency poison collar 62. In addition to the neutron shielding performed by walls 42, poison collar 62 further absorbs thermal neutrons which react with it to sharply define the thermal neutron flux passing through aperture 30. Poison collar 62 may be composed of any one or a combination of boron compound (B), cadmium (Cd), dysprosium (Dy), indium (In), or gadolinium (Gd) Preferably, collar 62 comprises a boron compound either alone or in combination with one of the elements above, as appropriate for the particular application of neutron radiography apparatus 10.

Figure 3:
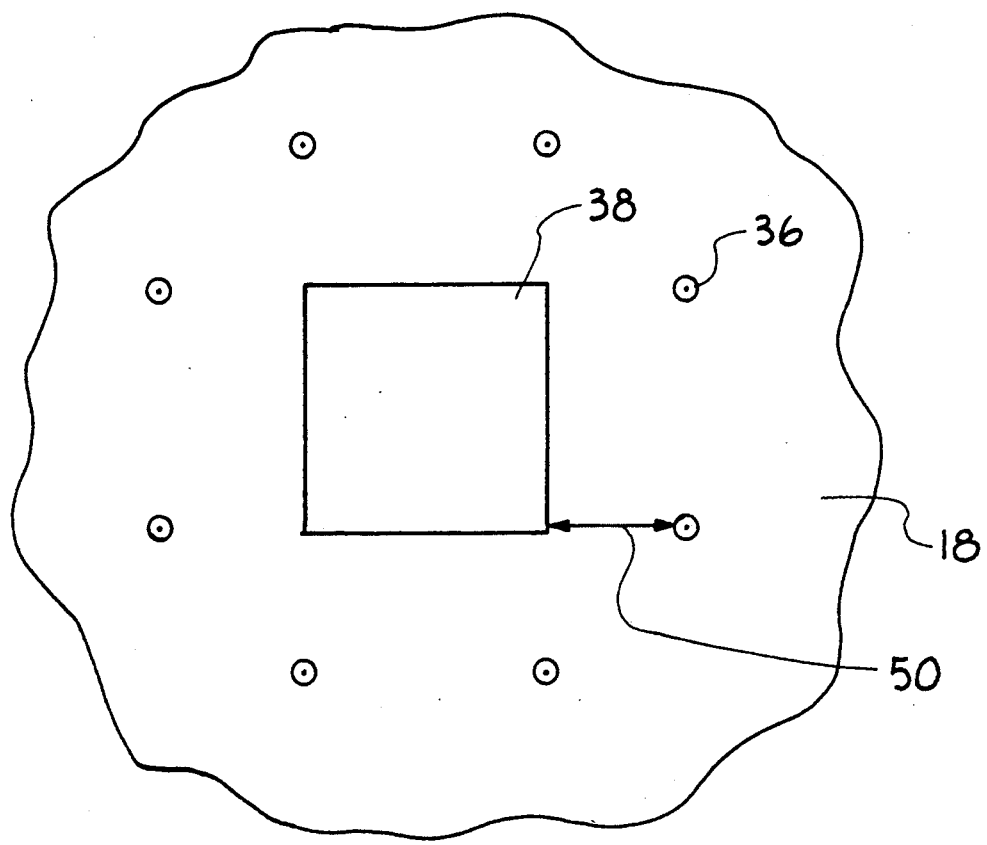
FIG. 3 is a cross-sectional plan view taken along line 3—3 of FIG. 2 of the neutron radiography apparatus shown in FIG. 2.

As further shown in FIGS. 2 and 3, the preferred source of neutrons, generally designated 36, is a radioisotope of californium-252 arranged in an array. The californium sources are symmetrically positioned about base 24, and are coplanar with base 24. This provides a source plane 38 of intense neutron flux. In particular, based on the structure shown, it is to be appreciated that the neutron sources 36 are positioned at a predetermined distance 50 from source plane 38. In addition, sources 36 are each also a predetermined distance 48 from aperture periphery 32. Thus, an optimum amount of moderator material 18 is positioned between each of the plurality of sources 36 and aperture periphery 32 to maximize the thermal neutron flux at source plane 38 and thence through aperture periphery 32. In the embodiment shown in FIG. 3, there are eight (8) neutron sources 36 arranged symmetrically and equidistant from one another in a substantially circular pattern. The source plane 38 is preferably in the shape of a square, having walls approximately four (4) inches in length. Each of the sources 36 are thus a distance 50 from the edge of source plane 38. In the preferred embodiment, distance 50 is approximately two (2) inches or about five (5) centimeters. Aperture 30, which is preferably also square in cross section, i.e. the same shape as base 24, has side lengths of approximately two (2) inches. In addition, the depth of converging collimator 20 is a distance 52 which, in the preferred embodiment, is also approximately four (4) inches.

Placement of the californium source at the distances prescribed takes advantage of the fact, well known in the art, that the thermal neutron flux in Be, BeO, $D_2O$, $H_2O$, and polyethylene as a function of distance from a neutron source, such as californium-252, is maximized between approximately four to ten (4–10) centimeters. Thus, the use of high density polyethylene as a moderator results in a maximum neutron flux at source plane 38 as a result of positioning the sources 36 as described herein. This increased intensity is further achieved by the greater separation between poison collar 62 and source plane 38, where maximum thermal neutron flux occurs.

In addition, it may readily be appreciated that due to the convergent-divergent collimator system used herein, thermal neutron flux from the full source plane 38, the source of thermal neutron flux, is directed toward imaging plane 16. Stated differently, the arrangement described herein results in imaging plane 16 being irradiated with thermal neutrons all of which emanate from the source region of highest intensity. This results in a uniform or equal distribution of neutrons across imaging plane 16. Also, the positioning of sources 36 described above prevents line-of-sight communication between the neutron sources 36 and the imaging plane 16. In other words, as shown by line-of-sight 54 from imaging plane 16 to source 36a, walls 42 of divergent collimator 40, which comprise neutron and gamma ray absorbers, substantially attenuate gamma rays produced directly by decay of neutron sources 36 which could otherwise irradiate imaging plane 16. Reducing the number of gamma rays which irradiate imaging plane 16 allows for greater contrast in the neutron-generated image of object 14.

In the preferred embodiment, the moderator material 18 is a cube with side lengths of approximately one (1) foot. Moderator 18 is preferably composed of high density polyethylene. Surrounding moderator material 18 is a neutron reflector 60 approximately three (3) feet on a side, which is preferably a polyethylene material. Reflector material 60 reflects a portion of the thermal neutrons back into moderator material 18 for further optimization of the thermal neutron flux available for radiography. Reflector material 60 is preferably also in the shape of a cube surrounding moderator material 18, and has dimensions of approximately three (3) feet by three (3) feet by three (3) feet, with the one (1) foot by one (1) foot by one (1) foot cube of moderator material 18 being contained therein.

It has also been recognized that thermal neutron irradiation of imaging plane 16 may be intensified by making aperture 30 and base 24 in the shape of a square, although other shapes could be utilized. It will also be appreciated by those skilled in the art that although an even number of sources 36 are used in the preferred embodiment shown, an odd number could also be used. Moreover, the angle "b" of the divergent collimator 40 as well as the angle "a" of convergent collimator 20 can be varied to accommodate the particular situation. For example, angle "a" of the walls of convergent collimator 20 could be the same, or slightly less than the angle "b" of divergent collimator 40, so that the full source plane, and only the full source plane, is within the direct line-of-sight of the imaging plane 16 through aperture 30. In addition to the above consideration, it is also anticipated that such angles would be chosen so as to prevent a direct line-of-sight between neutron sources 36 and imaging plane 16 through aperture 30, in order to reduce unwanted gamma ray irradiation of imaging plane 16. Moreover, the skilled artisan will recognize that another design consideration for the geometry of the collimators is the maximization of thermal neutron flux at source plane 38. To this end, it will be appreciated that as the volume of convergent collimator 20 is increased, the volume of moderator 18 is accordingly decreased, making less moderator available for thermalizing fast neutrons In addition to the considerations discussed above, it will also be appreciated by those skilled in the art that the present structure contemplates the use of cold neutrons and epithermal neutrons, as well as thermal neutrons, for generating a neutron radiographic image. The type of neutrons produced for imaging will depend on the particular material, design, and temperature chosen for moderator 18, as well as the composition of the detector making the radiograph image.

While the particular system and apparatus for neutron radiography as herein shown and disclosed in detail is fully capable of meeting the objectives and providing the advantages herein before stated, it is to be understood that it is merely illustrative of the presently preferred embodiments of the invention and that no limitations are intended to the details of construction or design herein shown other than as defined in the appended claims. For example, in applications of neutron radiography apparatus 10 which require cold neutrons for imaging, moderator 18 may be composed of cryogenically frozen methane surrounded by appropriate insulation.

I claim:

1. A neutron radiography apparatus, comprising:
an imaging plane;
a neutron moderator having a cavity defining a convergent collimator, said cavity having a base and converging walls of neutron moderating material terminating at an aperture;
a divergent collimator coaxially joined to said cavity at said aperture, said divergent collimator having diverging walls of radiation-absorbing material extending from said aperture to an expanded distal opening for irradiating said imaging plane;
a plurality of sources of neutrons disposed symmetrically about said base of said cavity;
a neutron moderating material disposed for maximum neutron thermalization between said sources and said base of said cavity; and
means for substantially shielding said plane from electromagnetic energy.

2. A neutron radiography apparatus as recited in claim 1, wherein said shielding means comprises:
said radiation-absorbing material being disposed between said sources and said imaging plane to substantially shield said imaging plane from electromagnetic radiation emanating from said source.

3. A neutron radiography apparatus as recited in claim 2, further comprising an electromagnetic radiation filter disposed within said base of said convergent collimator.

4. A neutron radiography apparatus as recited in claim 3, wherein said electromagnetic radiation filter comprises bismuth.

5. A neutron radiography apparatus as recited in claim 1, wherein said sources are positioned in the range of 4-10 centimeters from said aperture.

6. A neutron radiography apparatus as recited in claim 1, wherein said aperture is surrounded by neutron-absorbing material.

7. A neutron radiography apparatus as recited in claim 6, wherein said neutron-absorbing material comprises boron.

8. A neutron radiography apparatus as recited in claim 2, wherein said radiation-absorbing material comprises lead and boron.

9. A neutron radiography apparatus as recited in claim 1, wherein said sources comprises californium, americium-beryllium, or plutonium-beryllium.

10. A neutron radiography apparatus as recited in claim 1, wherein said aperture comprises a square approximately two inches in side length.

11. A neutron radiography apparatus as recited in claim 1, wherein said distal opening comprises a square approximately four inches in side length.

12. A neutron radiography apparatus as recited in claim 1, wherein said moderator comprises high density polyethylene.

13. A neutron radiography apparatus as recited in claim 1, wherein said moderator is surrounded by a layer of neutron-reflecting material.

14. A neutron radiography apparatus as recited in claim 13, wherein said reflecting material comprises polyethylene.

15. An apparatus for generating a neutron beam toward an imaging plane for neutron radiography, comprising:
a convergent collimator having a base and converging walls made of neutron moderating material, said walls extending from said base and converging toward a central axis terminating at an aperture periphery;

a divergent collimator coaxially joined with said convergent collimator and having diverging walls of neutron and electromagnetic radiation-absorbing material extending from said aperture toward an expanded distal opening for directing said neutron beam toward said imaging plane; and means for supporting a plurality of neutron sources symmetrically about said central axis to establish a source plane of neutron flux at said base, said sources being positioned at a distance from said base sufficient to achieve maximum cold, thermal, or epithermal neutron flux at said base, and being positioned at a location so that said neutron moderating material is interposed between said sources and said aperture, and so that said diverging walls of neutron and electromagnetic radiation-absorbing material are interposed between said sources and said imaging plane, said base being of sufficient size to expose substantially all of said imaging plane through said aperture to substantially all of said source plane.

16. A neutron radiography apparatus, comprising:

a collimator having a divergent portion formed with a divergent end for defining a neutron beam, a convergent portion having a base, and an aperture between said convergent and divergent portions;

an imaging plane disposed substantially within said neutron beam;

a plurality of sources of neutrons disposed symmetrically about said base of said convergent portion;

a neutron moderating material disposed for maximum neutron thermalization between said sources and said base of said convergent portion;

a neutron moderator surroundingly positioned against said collimator; and means for substantially shielding said imaging plane from electromagnetic energy.

17. A method for neutron radiography, comprising the steps of:

generating a cold, thermal, or epithermal neutron flux from a plurality of radioisotope neutron sources;

disposing an object defining an imaging plane within said flux;

directing said flux toward said imaging plane through a neutron moderator having a cavity defining a convergent collimator, said cavity having a base and converging walls of neutron moderating material terminating at an aperture;

a divergent collimator coaxially joined to said cavity at said aperture, said divergent collimator having diverging walls of radiation-absorbing material extending from said aperture to an expanded distal opening for irradiating said imaging plane, said sources being symmetrically disposed about said base of said cavity; and shielding said imaging plane from electromagnetic radiation.

* * * * *